United States Patent
Mangat et al.

(10) Patent No.: US 12,091,197 B2
(45) Date of Patent: Sep. 17, 2024

(54) AIRCRAFT FUEL SYSTEM MONITORING

(71) Applicant: AIRBUS OPERATIONS LIMITED, Bristol (GB)

(72) Inventors: Vikram Singh Mangat, Bristol (GB); Paul James Pilkington, Bristol (GB)

(73) Assignee: AIRBUS OPERATIONS LIMITED, Bristol (GB)

( * ) Notice: Subject to any disclaimer, the term of this patent is extended or adjusted under 35 U.S.C. 154(b) by 763 days.

(21) Appl. No.: 17/206,751

(22) Filed: Mar. 19, 2021

(65) Prior Publication Data
US 2021/0292009 A1 Sep. 23, 2021

(30) Foreign Application Priority Data
Mar. 19, 2020 (GB) ...................................... 2003970

(51) Int. Cl.
| | |
|---|---|
| B64F 5/00 | (2017.01) |
| B64D 37/02 | (2006.01) |
| B64F 5/60 | (2017.01) |
| G01F 23/263 | (2022.01) |
| G01N 33/28 | (2006.01) |

(52) U.S. Cl.
CPC ................ B64F 5/60 (2017.01); B64D 37/02 (2013.01); G01F 23/265 (2013.01); G01N 33/28 (2013.01)

(58) Field of Classification Search
USPC .............................................. 701/29.1–34.4
See application file for complete search history.

(56) References Cited

U.S. PATENT DOCUMENTS

| | | | | |
|---|---|---|---|---|
| 4,420,976 A | * | 12/1983 | Orloff ................... | G01F 23/266 |
| | | | | 73/304 C |
| 5,631,656 A | * | 5/1997 | Hartman ................. | G01S 1/026 |
| | | | | 701/30.6 |
| 6,157,894 A | | 12/2000 | Hess et al. | |
| 8,768,607 B2 | * | 7/2014 | Righi ..................... | B64D 37/00 |
| | | | | 701/1 |
| 2005/0165563 A1 | * | 7/2005 | Herbstreit .............. | B64D 37/00 |
| | | | | 702/55 |

(Continued)

FOREIGN PATENT DOCUMENTS

| | | | | |
|---|---|---|---|---|
| EP | | 3421951 B1 * | 8/2020 | ........... B64D 37/005 |
| JP | | 2018-079795 | 5/2018 | |

(Continued)

OTHER PUBLICATIONS

UK IPO Search Report and Written Opinion for GB2003970.7, dated Dec. 14, 2020, 10 pages.

Primary Examiner — Jonathan L Sample
(74) Attorney, Agent, or Firm — Nixon & Vanderhye P.C.

(57) ABSTRACT

An aircraft fuel system monitoring apparatus is disclosed having a processor configured to receive first information indicative of one or more parameters relating to fuel present in an aircraft; receive second information relating to the configuration of a fuel system of the aircraft; receive third information indicative of an orientation of the aircraft; receive fourth information indicative of a state of one or more non-fuel-related systems of the aircraft; and generate a prediction of a quantity of fuel present in the aircraft based on the received first information, the received second information, and one or both of the received third information and the received fourth information.

24 Claims, 3 Drawing Sheets

(56) References Cited

U.S. PATENT DOCUMENTS

| | | | | |
|---|---|---|---|---|
| 2006/0220890 | A1* | 10/2006 | Davis | G01F 23/802 |
| | | | | 340/612 |
| 2010/0017049 | A1* | 1/2010 | Swearingen | G07C 5/0816 |
| | | | | 701/31.4 |
| 2011/0224871 | A1* | 9/2011 | Sjungargard | B64D 37/00 |
| | | | | 701/36 |
| 2012/0296500 | A1* | 11/2012 | Yamasaki | B64C 13/00 |
| | | | | 701/14 |
| 2013/0245860 | A1* | 9/2013 | Cooper | B64D 45/00 |
| | | | | 701/14 |
| 2015/0151846 | A1* | 6/2015 | Haskins | B64D 37/32 |
| | | | | 244/135 R |
| 2017/0138776 | A1* | 5/2017 | Philiben | G01F 23/80 |
| 2018/0172571 | A1* | 6/2018 | Quartarone | G01F 23/18 |
| 2018/0299314 | A1* | 10/2018 | Zakrzewski | G01F 23/18 |
| 2018/0299318 | A1* | 10/2018 | Truong | B64D 37/005 |
| 2019/0003870 | A1* | 1/2019 | Quartarone | B64D 37/005 |
| 2019/0162573 | A1* | 5/2019 | Zahn | G01F 23/80 |
| 2020/0079522 | A1* | 3/2020 | Jomain | B64F 1/28 |
| 2021/0292009 | A1* | 9/2021 | Mangat | B64D 45/00 |

FOREIGN PATENT DOCUMENTS

| | | | | |
|---|---|---|---|---|
| KR | 10-2019-0115596 | | 10/2019 | |
| WO | WO-9932857 A1 | * | 7/1999 | ............. B64D 37/00 |
| WO | WO-0235185 A2 | * | 5/2002 | ........ G01F 23/0069 |
| WO | WO-2019079884 A1 | * | 5/2019 | ............. B64D 37/00 |

* cited by examiner

AIRCRAFT FUEL SYSTEM MONITORING

CROSS REFERENCE TO RELATED APPLICATION

This application claims priority to United Kingdom Patent Application GB 2003970.7, filed Mar. 19, 2020, the entire contents of which is hereby incorporated by reference.

TECHNICAL FIELD

The present invention relates to an aircraft fuel system monitoring apparatus, an aircraft comprising such an apparatus, and a method of predicting the quantity of fuel present in an aircraft.

BACKGROUND

It is very important for an aircraft operator to know accurately how much fuel is on board the aircraft at any given time, particularly since carrying more fuel than necessary is undesirable due to the additional weight this incurs. Fuel gauging systems in commercial aircraft typically estimate the current quantity of fuel in a given tank on the aircraft based on capacitance measurements from probes distributed around the tank, outputs from high and low fuel level sensors, measurements of the fuel properties, information about the current aircraft attitude, and height-volume tables for the particular fuel tank configuration.

SUMMARY

A first aspect of the present invention provides an aircraft fuel system monitoring apparatus. The monitoring apparatus comprises a processor configured to: receive first information indicative of one or more parameters relating to fuel present in an aircraft; receive second information relating to the configuration of a fuel system of the aircraft; receive third information indicative of an orientation of the aircraft; receive fourth information indicative of a state of one or more non-fuel-related systems of the aircraft; and generate a prediction of a quantity of fuel present in the aircraft based on the received first information, the received second information, and one or both of the received third information and the received fourth information.

Optionally, the first information comprises any one or more of: a first fuel height measurement for a first location in a fuel tank of the aircraft; a second fuel height measurement for a second location in a fuel tank of the aircraft; an output from a fuel level sensor; a fuel density measurement; a fuel temperature measurement; a fuel permittivity measurement.

Optionally, the first information comprises a measurement of one or more physical attributes of the fuel.

Optionally, the second information comprises any one or more of: details of the geometry of at least one fuel tank of the aircraft; details of the physical arrangement of the fuel system, a current status of one or more components comprised in the fuel system.

Optionally, the third information comprises values of one or more of: attitude, pitch, roll, acceleration, altitude, aircraft centre of gravity, aircraft speed.

Optionally, the fourth information comprises an indication of an aspect of the operational status of a non-fuel-related aircraft system. Optionally, the one or more non-fuel-related systems comprises any one or more of: a flight control system; a landing gear system; a cabin environmental system; a navigational system; a powerplant system.

Optionally, the processor is configured to use a machine learning algorithm to generate the prediction.

Optionally, the machine learning algorithm is a supervised machine learning algorithm.

Optionally, the machine learning algorithm has been trained using historical first information, historical second information, historical third information, and historical fourth information relating to a historical time period; and historical fifth information indicative of a fuel quantity present in one or more fuel tanks of the aircraft over the historical time period.

Optionally, each of the historical first information, the historical third information, the historical fourth information and the historical fifth information comprises data generated by the aircraft during its operation over the historical time period or data derived from data generated by the aircraft during its operation over the historical time period.

Optionally, the aircraft comprises multiple fuel tanks and the processor is configured to generate a prediction of a quantity of fuel present in each of the multiple fuel tanks.

Optionally, the aircraft comprises multiple fuel tanks and the processor is configured to generate a prediction of a total quantity of fuel present in the aircraft.

Optionally, the processor is further configured to:
receive fifth information indicative of a fuel quantity present in one or more fuel tanks of the aircraft; and
compare the generated prediction with the received fifth information.

Optionally, the processor is further configured to detect a fault associated with the fuel system, based on the results of the comparing.

Optionally, the processor is further configured to detect a fault associated with a non-fuel-related system of the aircraft, based on some or all of the received first, second, third and fourth informations.

Optionally, the processor is configured to detect the fault associated with the non-fuel-related system based on the received fifth information.

A second aspect of the invention provides a method of monitoring an aircraft fuel system. The method comprises:
receiving fuel property information relating to one or more physical properties of fuel present in an aircraft;
receiving fuel system configuration information relating to the physical arrangement of a fuel system of the aircraft;
receiving orientation information relating to the physical orientation of the aircraft;
receiving aircraft systems information relating to the state of at least one non-fuel-related system of the aircraft; and
determining a fuel quantity value indicative of a quantity of fuel present in the aircraft, based on the received fuel property information, the received fuel system configuration information, and one or both of the received orientation information and the received aircraft systems information.

Optionally, the method further comprises:
receiving fuel quantity information relating to an amount of fuel present in the aircraft;
comparing the received fuel quantity information with the determined fuel quantity value; and
detecting a fuel system fault based on the results of the comparing.

Optionally, the method further comprises: responsive to a positive detection of a fuel system fault, the fuel system using the determined fuel quantity value in place of a fuel quantity value calculated by the fuel system.

Optionally, the method further comprises: detecting a non-fuel aircraft system fault, based on the received aircraft systems information and one or more of the received fuel property information, the received orientation information, and the received fuel quantity information.

A third aspect of the invention provides an aircraft comprising a fuel system, and a monitoring apparatus according to the first aspect configured to monitor the fuel system.

Optionally, the processor of the monitoring apparatus is configured to perform the method of the second aspect.

BRIEF DESCRIPTION OF THE DRAWINGS

Embodiments of the invention will now be described, by way of example only, with reference to the accompanying drawings, in which.

DETAILED DESCRIPTION

The examples described herein relate to apparatus and methods for monitoring an aircraft fuel system. In each example, the monitoring uses first information indicative of one or more parameters relating to fuel present in an aircraft; second information relating to the configuration of a fuel system of the aircraft; third information indicative of an orientation of the aircraft; and fourth information indicative of a state of one or more non-fuel-related systems of the aircraft. Advantageously, monitoring apparatus and methods according to the invention can generate predictions of a quantity of fuel present in an aircraft, which are independent from a determination of a fuel quantity amount generated by a primary fuel quantity indication/gauging system of that aircraft. Some of the example monitoring apparatus and methods may additionally be able to detect faults with a fuel system of the aircraft and/or with a non-fuel related system of the aircraft.

Figure 1:
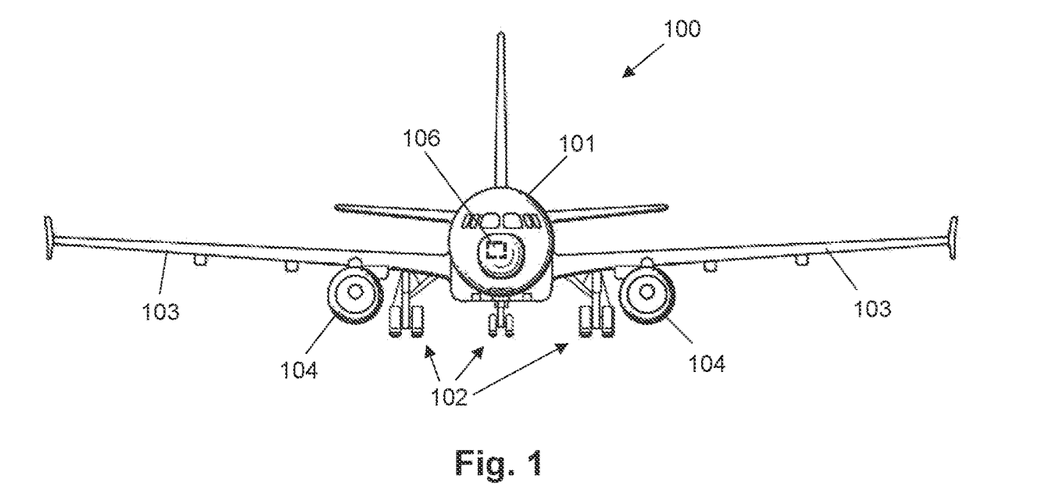
FIG. 1 is a front view of an example aircraft comprising a monitoring apparatus according to the invention.

FIG. 1 is a simplified schematic view of an aircraft 100. The aircraft 100 comprises a fuselage 101, a pair of wings 103, a pair of engines 104, and a plurality of landing gear assemblies 102. The aircraft 100 further comprises a computing system 106 which may, for example, comprise one or more processors and one or more computer readable storage media. The aircraft 100 may also comprise instruments or sensors for measuring characteristics or parameters related to the aircraft, and instruments or sensors for measuring environmental characteristics, which may be distributed at various different locations on the aircraft 100. The aircraft 100 may also comprise indicating devices for providing various indications relating to the aircraft. The indicating devices may include screens which display text and/or graphics, dials, light indicators, sound indicators which emit sound to provide indications, and the like.

The aircraft 100 comprises a plurality of fuel tanks (not visible) and a fuel distribution system for transporting fuel from the tanks to the engines 104. For example, the fuel tanks may comprise sealed compartments at least partly formed by the structure of the wings 103, and/or the fuselage 101, and/or any other part of the aircraft 100. The aircraft 100 further comprises a fuel system (not visible) for determining a quantity of fuel contained in the fuel tanks of the aircraft 100. The aircraft 100 may further comprise a fuel property sensing system (not visible) configured to measure characteristics of uplifted fuel during refuelling operations.

The fuel system comprises various sensors. Several types of sensor are known in the prior art which are suitable for measuring the quantity of fuel in an aircraft tank. The type of sensor most commonly used for commercial airliners is a capacitive probe comprising two electrodes in the form of coaxially arranged cylindrical tubes. The capacitive probe is open at both ends so that fuel can freely enter the space between the electrodes. The capacitance of the capacitor formed by the two electrodes depends linearly on the height of the fuel column between the two tubular electrodes. A measured capacitance value therefore correlates with the amount by which the probe is immersed in fuel, and consequently also with the fuel level at the location of the probe.

A capacitive fuel gauging system on-board an aircraft typically comprises multiple capacitive probes installed at predetermined heights at predetermined distributed locations within each fuel tank of the aircraft; and at least one controller connected to the probes. The controller is configured to calculate the quantity of fuel that each tank contains, based on the capacitance values measured by the probes together with stored information about the geometric characteristics of the fuel tanks. Such a fuel gauging system may also comprise one or more auxiliary sensors installed in each of the fuel tanks, which are not involved in the primary calculation of fuel quantity. Such auxiliary sensors may include for example (in respect of each fuel tank): at least one high level detector; at least one low level detector; a water sensor; a temperature sensor; a permittivity sensor. Each auxiliary sensor is connected to the controller, which is configured to process measurement data generated by the auxiliary sensors.

Figure 2:
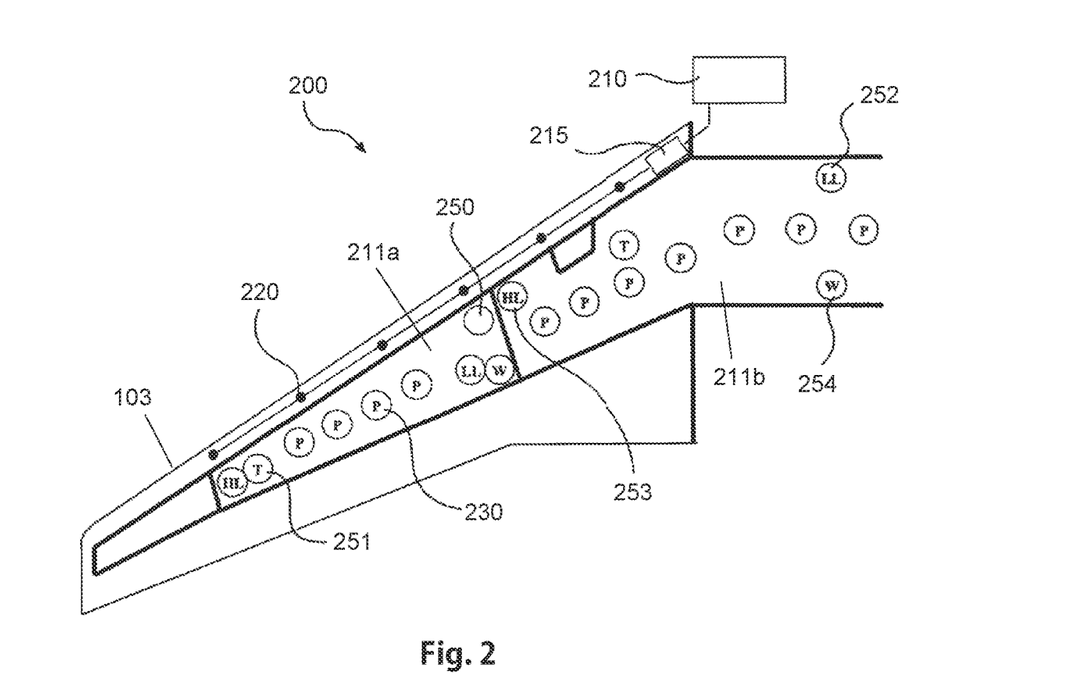
FIG. 2 is a schematic diagram depicting part of a fuel system of the aircraft of FIG. 1.

FIG. 2 diagrammatically illustrates part of an example fuel system 200 suitable for use on-board the aircraft 100. In particular, a part of the fuel system 200 associated with fuel tanks 211a, 211b located in a port-side half of an aircraft is shown. A further part of the fuel system 200, which is not shown, is associated with fuel tanks located in a starboard-side half of the same aircraft. The further (starboard-side) part of the fuel system may be substantially similar to the illustrated (port-side) part. The fuel system 200 comprises a fuel quantity indication (FQI) controller 210, a plurality of local controllers 220, a plurality of capacitive probes 230 (labelled P), as well as a plurality of auxiliary sensors 250. In the particular illustrated example, the fuel system 200 further comprises at least one data concentrator 215, although this need not be the case in other examples. Each local controller 220 is connected to a plurality of capacitive probes 230, as well as to one or more of the auxiliary sensors 250 that are located in the vicinity of that local controller 220. The data processed by some or all of the local controllers 220 is grouped together by the data concentrator 215 before being transmitted to the FQI controller 210.

The capacitive probes 230 may be of any suitable design known in the art. Each capacitive probe 230 is installed in one of the fuel tanks 211a, 211b at a predetermined height and at a predetermined location. As explained above, the capacitance value measured by a given probe 230 varies according to how much of that probe is immersed in fuel. Thus, each capacitance measurement can be used to derive a fuel level (relative to the tank) at the location of the probe 230 which acquired that measurement.

The FQI controller 210 receives measured capacitance values from the probes 230, via the local controllers 220 and the data concentrator 215. The FQI controller 210 is configured to calculate the quantity of fuel in each tank 211a, 211b based on capacitance measurements provided by the capacitive probes 230 in that tank, and on information relating to the geometry of that tank. The FQI controller 210 is in communication with a data storage medium (such as a computer memory device) on which information relating to the configuration of the fuel system 200 is stored, including details of the geometry of each fuel tank 211a, 211b comprised in the fuel system 200. The FQI controller 210 may additionally base the calculation of fuel quantity on orientation information which is indicative of an orientation of the aircraft. Such information may include, for example, current measurements of the attitude, pitch, roll and/or acceleration of the aircraft. The FQI controller 210 may receive such orientation information from a further system of the aircraft 100 (such as an Air Data Inertial Reference System (ADIRS)).

The geometry of the fuel tank, aircraft orientation information, and capacitance measurements obtained by the probes 230 in that tank are combined by the FQI controller 210 to determine a height and angle of the fuel surface relative to the fuel tank (assuming a planar fuel surface). The FQI controller 210 is configured to then determine a fuel mass or fuel volume using a predefined look-up table linking fuel mass/volume to fuel height and angle, which is stored on the data storage medium. The FQI controller 210 is configured to then send the determined fuel quantity to one or more indicating devices of the aircraft, so that it is available to the crew.

The plurality of auxiliary sensors 250 includes (in respect of each fuel tank) at least one temperature sensor 251 (labelled T), at least one low level sensor 252 (labelled LL), at least one high level sensor 253 (labelled HL) and at least one water sensor 254 (labelled W). The low level sensors 252 are placed in the lowest positions of the fuel tanks 211a, 211b and the high level sensors 253 are arranged in positions above which overflow into a surge tank would happen. The auxiliary sensors 250 may utilise any suitable sensing technology known in the art. The FQI controller 210 processes the measurements coming from the auxiliary sensors 250 and transmits, if applicable, control signals to one or more indicating devices of the aircraft (such as an in-flight alarm system).

Figure 3:
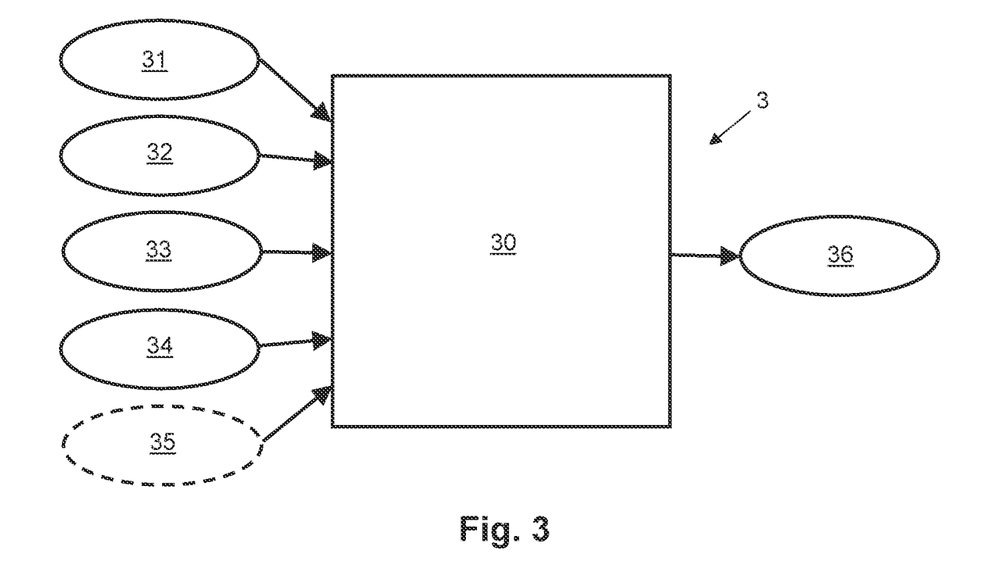
FIG. 3 is a schematic block diagram of an example monitoring apparatus according to the invention.

The aircraft 100 further comprises a fuel system monitoring apparatus according to the invention. FIG. 3 shows an example fuel system monitoring apparatus 3 according to the invention which is suitable for use on the aircraft 100. The monitoring apparatus 3 may, for example, monitor one or more aspects of the operation of the fuel system 200 of FIG. 2. The system 3 comprises a processor 30 which is configured to receive first information 31, second information 32, third information 33 and fourth information 34, and to generate a prediction 36 of a quantity of fuel present in the aircraft 100 based on the received first information 31, the received second information 32, and one or both of the received third information 33 and the received fourth information 34. Optionally, the processor 30 is further configured to also receive fifth information 35. The first, second, third, fourth and fifth informations 31, 32, 33, 34 are all different from each other in terms of the nature of the information and/or the source of the information. The first information 31 is indicative of one or more parameters relating to fuel present in the aircraft 100. The second information 32 relates to the configuration of a fuel system 200 of the aircraft 100. The third information 33 is indicative of an orientation of the aircraft 100. The fourth information 34 is indicative of a state of one or more non-fuel-related systems of the aircraft 100. The fifth information is indicative of a fuel quantity present in one or more fuel tanks 211a, 211b of the aircraft 100.

The first information 31 is indicative of one or more parameters relating to fuel present in an aircraft (hereinafter referred to as "fuel parameters"). The parameters may correspond to physical properties or attributes of the fuel. In some examples the first information 31 comprises measurement data, such as a measured value of at least one fuel parameter. Some of the first information 31 may comprise current measured values of one or more fuel parameters. "Current" is intended to mean that the measured value was obtained substantially immediately prior to being used by the processor 30 to generate a prediction 36. There may inevitably be a small delay between obtaining a measurement value and generating a prediction 36 based on that measurement value, due to the time required to transmit the data and perform the processing, but this delay is not considered to render the measurement value non-current. Parameters which comprise current values may be, for example, those parameters which the fuel system 200 is configured to measure in-flight.

Some of the first information 31 may comprise non-current values of one or more fuel parameters, for example parameter values measured during the most recent refuelling process for the aircraft 100. Such parameters may be, for example, parameters which are measured by the FPMU of the aircraft 100 during refuelling but are not measured by the fuel system 200 during flight of the aircraft 100. Such measurement values are not considered to be current (however; nor are they considered to be "historical", as will be explained in more detail below). The first information 31 comprises up-to-date non-current values, where "up-to-date" means that those values are the most recently measured values of the particular parameter(s).

The first information may comprise any one or more of: a first fuel height measurement for a first location in a fuel tank of the aircraft; a second fuel height measurement for a second location in a fuel tank of the aircraft; an output from a fuel level sensor; a fuel density measurement; a fuel temperature measurement; a fuel permittivity measurement. A fuel height measurement may comprise any measurement indicative of a fuel height at a given location within a fuel tank. For example, a fuel height measurement may comprise a measured capacitance; a measured pressure; a measured height; or any other measurement from which fuel height at a location in a fuel tank may be derived. The fuel parameter (s) of which the first information 31 is indicative may include any or all of: fuel temperature; fuel permittivity; fuel density; fuel level relative to a fuel tank; fuel pressure. The first information 31 may comprise direct measurements of these parameters, or measurements of one or more other parameters (such as capacitance) from which a fuel parameter value can be derived. The first information 31 may include measured values (e.g. of capacitance) which are used by the fuel system 200 to determine a fuel quantity value, in the manner described above in relation to FIG. 2.

The first information 31 may be obtained by a sensor/probe comprised in the fuel system 200, and or by a sensor/probe comprised in the fuel property sensing system, and/or by any other sensor comprised in the aircraft 100 that is suitable for obtaining measurement information from which a fuel parameter is directly or indirectly derivable. The first information 31 may be transmitted to the processor 30 via a communications link. In such examples the processor 30 may receive the first information 31 directly from a sensor which generates the information, from a further controller comprised in the aircraft 100 (such as one of the local controllers 220, the FQI controller 210, or a controller associated with the fuel property sensing system). Alternatively the processor 30 may retrieve the first information 31 from a computer readable storage medium. At least some of the first information 31 may be received by the processor 30 at one or more discrete times during a flight cycle of the aircraft 100. For example, some of the first information 31 may be received by the processor at the end of a refuelling process. At least some of the first information 31 may be continuously received by the processor 30 during an operational period of the aircraft 100.

The received second information 32 may be any information which relates to the configuration of the fuel system 200 of the aircraft 100. The second information 32 may comprise details of the geometry of the fuel tanks 211a, 211b of the aircraft 100. The second information may comprise static information (where static means that it does not change during operation of the aircraft), which is pre-loaded onto a computer readable storage medium accessible by the processor 30. Fuel tank geometry is an example of such static information. In such examples the second information 32 is not generated by any sensor on-board the aircraft. The second information 32 may remain valid for the operational lifetime of the aircraft 100 (or a significant part thereof). The second information 32 may comprise information relating to the physical arrangement of the fuel system 200 (such as the location and type of various components). The second information 32 may comprise information relating to components comprised in the fuel system 200, such as pumps and valves. The second information 32 may comprise current information which is indicative of a current status (e.g. closed or open, operational or non-operational) of one or more components comprised in the fuel system 200. Such current information may be received by the processor 30 via a direct or indirect communications link to the component(s). Current second information 32 may be received according to any of the same general principles as current first information 31.

The received third information 33 (which is indicative of a physical orientation, position and/or state of motion of the aircraft 100) may comprise values of one or more top-level flight parameters, such as attitude, pitch, roll, acceleration, altitude, aircraft speed, aircraft centre of gravity (CoG) and the like. Some of the third information 33 may comprise current values of the one or more top-level flight parameters. The third information 33 may comprise parameter values which have been measured and/or derived by a further system of the aircraft 100 (such as an ADIRS). The third information 33 may comprise orientation information which is used by the fuel system 200 to determine a quantity of fuel present in the aircraft 100. The third information 33 may be transmitted to the processor 30 via a communications link. In such examples the processor 30 may receive the third information 33 directly from a sensor which generates at least some of the information, or from a further controller comprised in the aircraft 100 (such as a controller of an ADIRS), or the processor 30 may retrieve the third information 33 from a computer readable storage medium. At least some of the third information 33 may be received by the processor 30 at one or more discrete times during a flight cycle of the aircraft 100. At least some of the third information 33 may be continuously received by the processor 30 during an operational period of the aircraft 100.

The received fourth information 34 may be any information which is indicative of a state of a non-fuel-related system of the aircraft 100. A non-fuel-related system is considered to be any aircraft system not configured for storing, monitoring, distributing, measuring, indicating or performing any other function in relation to fuel present in the aircraft 100. Examples of non-fuel-related systems are flight control systems (e.g. flaps, ailerons, spoilers, horizontal tail plane, vertical tail plane and the like), cabin environmental systems, navigational systems, powerplant systems and landing gear systems. A state of a system may be operational or non-operational. A state of a system may be a current operational configuration (such as retracted or deployed, for a landing gear system; or a specific combination of positions and orientations of moveable control surfaces of the aircraft, for a flight control system). Any aspect of the operational status of a non-fuel-related aircraft system which it is possible to define as a specific state may be indicated by the received fourth information 34.

The received fifth information 35, which is optional and therefore need not be received by the processor 30 all examples of the invention, is indicative of an amount of fuel (that is, a fuel quantity) present in the aircraft 100. The fifth information 35 may comprise a value of a fuel volume or mass present in a particular fuel tank of the aircraft 100. The fifth information 35 may comprise such a fuel volume or mass value for each fuel tank of the aircraft 100. The fifth information 35 may comprise a fuel quantity value determined by the fuel system 200. The fifth information 35 may be received from the fuel system 200 (or more particularly, from the FQI controller 210).

The processor 30 may be located in an avionics bay of the aircraft 100. It may form part of the computing system 106. The processor 30 may be in communication with any or all of: one or more computer readable storage media, one or more sensors, one or more output devices, and/or one or more other aircraft systems, as required for the processor 30 to receive the first, second, third, fourth and (optionally) fifth informations 31, 32, 33, 34, 35, and to generate a prediction 36 of a quantity of fuel present in the aircraft 100.

The processor 30 is configured to use a machine learning algorithm to generate the prediction 36 of a fuel quantity present in the aircraft 100. Machine learning is a form of data analysis in which a model is automatically created by an algorithm, based on the algorithm identifying patterns in training data without being given any explicit instructions. Machine learning algorithms may be supervised, meaning that the algorithm is configured to infer a function from training data comprising labelled example input-output pairs, or unsupervised, meaning that the algorithm is configured to find previously unknown patterns in an unlabelled data set. The machine learning algorithm used by aircraft fuel system monitoring apparatuses according to the invention is a supervised machine learning algorithm.

The machine learning algorithm implemented by the processor 30 has been trained using historical first information, historical second information, historical third information, and historical fourth information relating to a historical time period; as well as historical fifth information indicative of a fuel quantity present in each of the fuel tanks 211a, 211b of the aircraft 100 over the historical time period. The historical time period may end at the current time. The historical time period may end at the completion of the last (that is, most recent) flight cycle of the aircraft 100. The historical time period may begin at the time of the entry into service of the aircraft 100. The historical time period may begin at the time of the first flight of the aircraft 100. The historical time period may begin at any time between the current time and the time of the first flight of the aircraft 100.

The historical first, second, third, fourth and fifth informations may be substantially the same as the received first, second, third, fourth and fifth informations 31, 32, 33, 34 described above, except that the historical informations relate to the historical time period whereas the received informations relate to the current time (that is, the time at which the processor 30 is generating a prediction). Where some of the received information comprises static information (such as fuel tank geometry), that part of the received information may be the same as the same part of the historical information. At least some of the historical informations may comprise out-of-date received informations. Historical information used to train the machine learning algorithm may, in some examples, be stored on a computer readable storage medium accessible by the processor 30.

In some examples the fuel system monitoring apparatus 3 may undergo a training period before it begins operating to generate predictions 36 of a quantity of fuel present in the aircraft 100. The training period may be the same as (that is, simultaneous with and of equal duration to) the historical time period. The training period may encompass the historical time period. The training period may occur after the historical time period. During the training period, the machine learning algorithm may operate to determine relationships between the first, second, third, fourth and fifth historical informations, but not to generate predictions 36 of a quantity of fuel present in the aircraft 100, or to perform any other predictive or diagnostic function.

The manner in which an amount of fuel present in an aircraft changes during a flight is dependent on various factors, which include but are not limited to: the type of the aircraft, the configuration of the fuel system, physical properties of the fuel, external environmental conditions (such as wind speed and direction, temperature, altitude, aircraft speed and the like), the route taken by the aircraft, how the flight control surfaces are used, how the aircraft's engines are used, flight phase. The received first, second, third, and fourth informations are all indicative of parameters which are expected to correlate with the actual amount of fuel present in the aircraft at a given time, and/or to affect the rate at which the aircraft uses fuel. Some of the received first, second, third and fourth informations may be related, directly or indirectly, to factors (such as those listed above) on which an amount of fuel (or the variation of that amount) present in an aircraft is dependent, and/or on which a rate at which the aircraft uses fuel is dependent.

During the training process, the machine learning algorithm will have "learnt" associations between the various parameters indicated by the information used to train it, such that it became able to generate a prediction 36 of a quantity of fuel currently present in the aircraft based on up-to-date (not historical) first information 31, second information 32, and one or both of third information 33 and fourth information 34. According to the nature of machine learning algorithms, the details of these learned associations and the manner in which the prediction is generated remain opaque to the operator. In some examples the machine learning algorithm does not require both third information 33 and fourth information 34 to generate a fuel quantity prediction 36. That may be because, in these examples, the fourth information 34 comprises parameters which are correlated with the orientation of the aircraft 100, and/or comprises parameters from which the orientation of the aircraft 100 can be derived. For example, the state of the flight-control surfaces is expected to correlate with the orientation of the aircraft 100 during flight. The state of the landing gear may also correlate with the orientation of the aircraft 100, since the landing gear is only ever deployed when the aircraft 100 is on the ground (and therefore substantially level) or for short periods during the take-off and landing phases. It is not necessary for a correlation between parameters to be straightforward, well-understood, well-defined, or even known in advance to exist, in order for the machine learning algorithm to learn and utilise it in generating a fuel quantity prediction 36.

Thus, the processor 30 generating a prediction of a quantity of fuel present in the aircraft 100 comprises the machine learning algorithm operating on the received first information 31, the received second information 32, and one or both of the received third information 33 and the received fourth information 34, to generate the prediction 36. The fuel quantity prediction 36 output by the machine learning algorithm may comprise a prediction of a mass or volume of fuel currently present in a given fuel tank 211a, 211b of the aircraft 100. The fuel quantity prediction 36 may comprise a prediction of a mass or volume of fuel currently present in each fuel tank 211a, 211b of the aircraft 100. The fuel quantity prediction 36 may comprise a prediction of a total mass or volume of fuel currently present in the aircraft 100. The fuel system monitoring apparatus 3 may be configured to send the prediction 36, in any suitable format, to a further system of the aircraft such as a display device or an indicating device.

The fuel quantity prediction 36 generated by the processor 30 is generated independently from a fuel quantity determined by the FQI controller 210. The prediction 36 can therefore provide a back-up indicator of fuel quantity, available to be used in the event of a failure of a primary fuel quantity determination system (comprised in the fuel system 200). The prediction 36 can also be used as the basis for detection of a fault with the fuel system 200. To this end, in some examples the processor 30 is configured to receive fifth information 35 which comprises the output of a primary fuel quantity determination system of the aircraft 100, and to compare the generated prediction 36 with the received fifth information 35. If there is a significant discrepancy between a fuel quantity indicated by the received fifth information 35 and the equivalent fuel quantity predicted by the processor 30, the processor 30 may be configured to determine that there exists a fault associated with the fuel system 200. The processor 30 may be preprogramed with predefined rules to determine whether or not a discrepancy is significant. In the event a significant discrepancy is detected, the processor 30 may be configured to send a signal to an indicating device of the aircraft 100 to alert the crew. In some examples the processor 30 is configured such that, if a significant discrepancy is detected (that is, a positive detection of a fault associated with the fuel system 200 is made), the processor transmits the generated prediction 36 to the FQI controller 210 of the fuel system 200. In such examples, the FQI controller 210 may be configured to use the generated prediction 36 instead of a corresponding fuel quantity value calculated by the FQI controller 210. This enables fuel gauging accuracy to be maintained at a high level even when there exists a fault with the fuel system 200.

In some examples, the processor 30 may be configured to localize and/or identify a detected fault with the fuel system 200. The processor 30 may perform the localization and/or identification based on any or all of the received first, second, third, fourth and fifth informations 31, 32, 33, 34, 35. In some examples the processor 30 is configured to receive sixth information indicative of an operational status of one or more components of the fuel system 200. In such examples the processor 30 may perform the localization and/or identification (or additionally based) on the received sixth information. The localization and/or identification may be performed using a further machine learning algorithm of substantially the same type as the machine learning algorithm used by the processor 30 to generate the fuel quantity prediction 36. The further machine learning algorithm may have been trained using historical sixth information relating to the aircraft 100 and the historical time period (as well as one or more of the historical first, second, third, fourth and fifth informations). However; given that faults associated with the fuel system 200 are expected to be rare, the further machine learning algorithm may have been trained using a larger set of training data than that which is available for the particular aircraft 100 over the historical time period. The training data may comprise, for example, historical sixth information (and one or more of historical first, second, third, fourth and fifth informations) which relates to multiple aircraft of the same design as the aircraft 100 and having the same type of fuel system 200, and which covers a longer time period than the historical time period.

In some examples the processor 30 is configured to detect a fault associated with a non-fuel-related system, the state of which is indicated by the received fourth information 34. The processor 30 may be configured to detect a fault associated with a non-fuel-related system based on the received fourth information 34 and one or more of the received first, second, third and fifth informations 31, 32, 33, 35. For example, the machine learning algorithm may learn relationships between the received fourth information 34 and some other part of the received information. For instance, fourth information 34 indicative of the state of a flight control system of the aircraft 100 is expected to be related to the orientation of the aircraft 100 in a manner that will be learnt by the machine learning algorithm during the training period and/or during subsequent operation of the monitoring apparatus 3. Various other analogous relationships will exist and will be learnable by the machine learning algorithm. In some examples the processor 30 is configured to detect a significant deviation from any of these learned relationships. The processor 30 may be preprogramed with predefined rules to determine whether or not a deviation is significant. In the event a significant deviation is detected, the processor 30 may be configured to send a signal to an indicating device of the aircraft 100 to alert the crew. Such a signal may contain information about which non-fuel-related system the deviation relates to, to assist the crew in localizing and identifying the fault.

Figure 4:
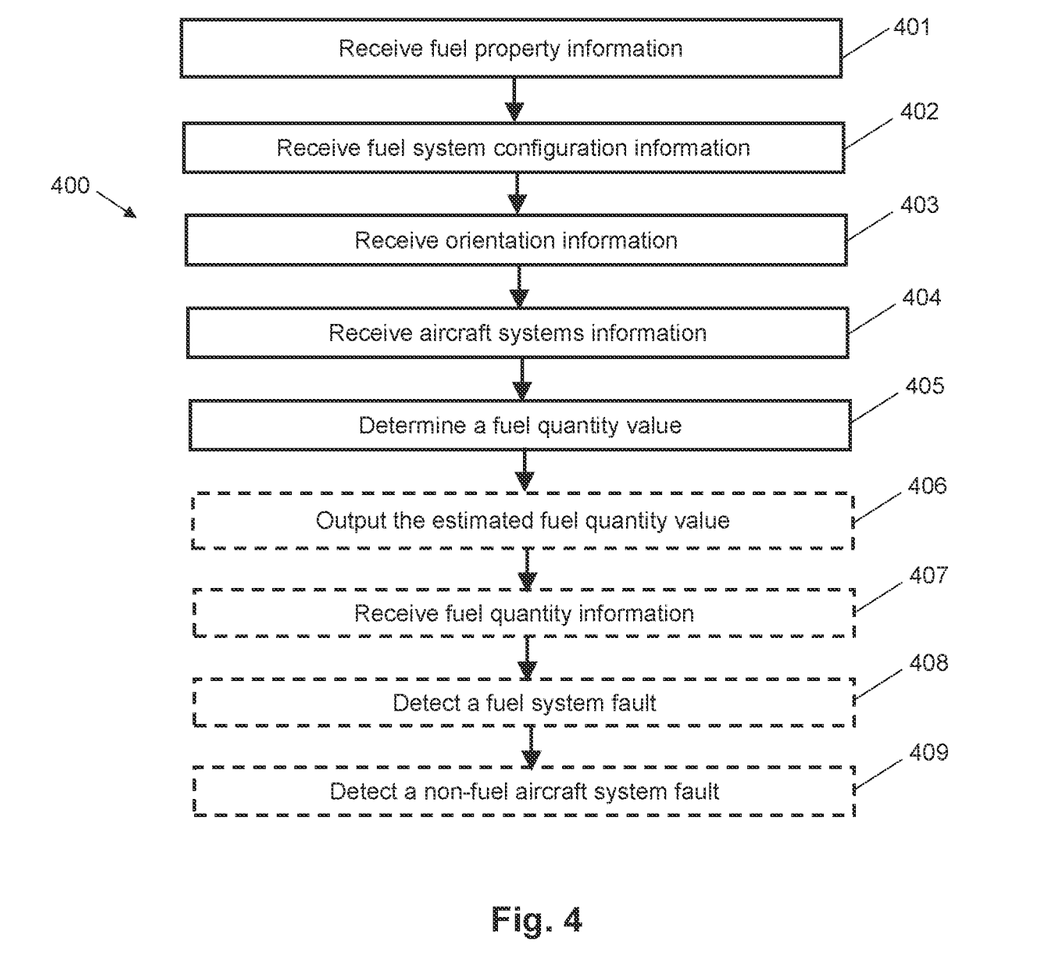
FIG. 4 is a flow chart illustrating an example method according to the invention.

FIG. 4 is a flow chart illustrating an example method 400 of monitoring an aircraft fuel system. The aircraft fuel system may be, for example, the example fuel system 200 of the example aircraft 100 discussed above. The method may be implemented by an aircraft fuel system monitoring apparatus, such as the example monitoring apparatus 3 described above.

A first block 401 of the method 400 comprises receiving fuel property information relating to one or more physical properties of fuel present in an aircraft. The fuel property information may have any of the features of the first information 31 discussed above in relation to the monitoring apparatus 3, and it may be received in an equivalent manner. A second block 402 of the method 400 comprises receiving fuel system configuration information relating to the physical arrangement of a fuel system of the aircraft. The fuel system configuration information may have any of the features of the above-described second information 32, and it may be received in an equivalent manner. A third block 403 of the method 400 comprises receiving orientation information relating to the physical orientation of the aircraft. The orientation information may have any of the features of the above-described third information 33, and it may be received in an equivalent manner. A fourth block 404 of the method 400 comprises receiving aircraft systems information relating to the state of at least one non-fuel-related system of the aircraft. The aircraft systems information may have any of the features of the above-described fourth information, and it may be received in an equivalent manner. Blocks 401-404 may be performed by a processor of an aircraft fuel system monitoring apparatus, such as the example processor 30. Any two or more of blocks 401-404 may (but need not) be performed simultaneously.

In block 405, a fuel quantity value indicative of a quantity of fuel present in the aircraft is determined, based on the received fuel property information, the received fuel system configuration information, and one or both of the received orientation information and the received aircraft systems information. The determination may be performed by a processor, for example in the manner described above in relation to the operation of the processor 30 of the example monitoring apparatus 3. The determination may be performed using a machine learning algorithm. Block 405 may be performed periodically or continuously during a time that the aircraft is operational. For example, if blocks 401-404 are performed continuously such that a continuous stream of up-to-date information is available, then block 405 may be performed continuously, to generate a continuous stream of up-to-date fuel quantity values. On the other hand, if any of blocks 401-404 are performed intermittently, then block 405 may only be performed when up-to-date information is available for all of the types of received information.

The method 400 may further comprise any or all of four optional blocks 406 to 409. However; block 408 is dependent on block 407 having occurred, so examples of the method which comprise optional block 408 must also comprise optional block 407.

In optional block 406, the determined fuel quantity value (that is, the value determined as a result of performing block 405) is output. Outputting the determined fuel quantity value may comprise a processor which performed the determination sending a signal to a further system or device. Such a signal may be configured, for example, to cause the further system or device to display or otherwise indicate the determined fuel quantity value, or to display or otherwise indicate some other information based on or derived from the determined fuel quantity value. Alternatively or additionally, the signal may be configured to be used by the further system or device as an input to a further process. The outputting may be performed any suitable techniques known in the art. Block 406 may be performed whenever an up-to-date fuel quantity value has been determined in block 405. In some examples, block 405 may only be performed when an up-to-date determined fuel quantity value differs from the most recent out-of-date determined fuel quantity value.

In optional block 407, fuel quantity information relating to an amount of fuel present in the aircraft is received. The fuel quantity information may have any of the features of the fifth information 35 discussed above in relation to the monitoring apparatus 3, and it may be received in an equivalent manner.

In optional block 408, a fuel system fault is detected. The detecting may comprise comparing the fuel quantity information received in block 407 with the fuel quantity value determined in block 405, and detecting a fuel system fault based on the results of the comparing. In such examples, the performance of optional block 408 requires optional block 407 to have already been performed. The detection may be performed by the processor, for example in the manner described above in relation to the operation of the processor 30 of the example monitoring apparatus 3. The detection may be performed using a machine learning algorithm, which may be (but need not be) the same machine learning algorithm that performs the determination of the fuel quantity value in block 405. Performance of block 408 may result in either a positive detection (that is, a fault is found) or a negative detection (that is, no fault is found). Block 408 may be performed each time a new fuel quantity value is determined. Block 408 may be performed periodically or continuously during a time in which the aircraft is operational. Responsive to a positive detection, a signal may be transmitted to an indication system of the aircraft, and/or to a controller of the fuel system. In some examples a signal transmitted to the controller of the fuel system responsive to a positive detection of a fault associated with the fuel system may cause the fuel system to use the fuel quantity value determined in block 405 instead of a fuel quantity value calculated by the fuel system.

In optional block 409, a non-fuel aircraft system fault (that is, a fault associated with a non-fuel-related system of the aircraft) is detected based on the received aircraft systems information and one or more of the received fuel property information and the received orientation information (and, if optional block 407 has been performed, the received fuel quantity information). The detection may be performed by the processor, for example in the manner described above in relation to the operation of the processor 30 of the example monitoring apparatus 3. The detection may be performed using a machine learning algorithm. Performance of block 409 may result in either a positive detection (that is, a fault is found) or a negative detection (that is, no fault is found). Block 409 may be performed periodically or continuously during a time in which the aircraft is operational.

Although the invention has been described above with reference to one or more preferred examples or embodiments, it will be appreciated that various changes or modifications may be made without departing from the scope of the invention as defined in the appended claims.

Although the invention has been described above mainly in the context of a capacitance-based fuel gauging system, it may also be advantageously applied to other types of fuel systems such as pressure-based fuel gauging systems and ultrasound-based fuel-gauging systems. That is, the monitoring apparatus and methods according to the invention may be used to monitor any form of aircraft fuel gauging system, irrespective of the technology used by that fuel gauging system.

Although the invention has been described above mainly in the context of a fixed-wing aircraft application, it may also be advantageously applied to various other applications, including but not limited to applications on vehicles such as helicopters, drones, trains, automobiles and spacecraft.

Where the term "or" has been used in the preceding description, this term should be understood to mean "and/or", except where explicitly stated otherwise.

The invention claimed is:

1. An aircraft fuel system monitoring apparatus, comprising a processor configured to:
receive first information indicative of one or more parameters relating to fuel present in an aircraft;
receive second information relating to the configuration of a fuel system of the aircraft;
receive third information indicative of an orientation of the aircraft;
receive fourth information indicative of a state of one or more non-fuel-related systems of the aircraft; and
generate a prediction of a quantity of fuel present in the aircraft based on the received first information, the received second information, and one or both of the received third information and the received fourth information.

2. A monitoring apparatus according to claim 1, wherein the first information comprises any one or more of: a first fuel height measurement for a first location in a fuel tank of the aircraft; a second fuel height measurement for a second location in a fuel tank of the aircraft; an output from a fuel level sensor; a fuel density measurement; a fuel temperature measurement; a fuel permittivity measurement.

3. A monitoring apparatus according to claim 1, wherein the first information comprises a measurement of one or more physical attributes of the fuel.

4. A monitoring apparatus according to claim 1, wherein the second information comprises any one or more of: details of the geometry of at least one fuel tank of the aircraft; details of the physical arrangement of the fuel system, a current status of one or more components comprised in the fuel system.

5. A monitoring apparatus according to claim 1, wherein the third information comprises values of one or more of: attitude, pitch, roll, acceleration, altitude, aircraft centre of gravity, aircraft speed.

6. A monitoring apparatus according to claim 1, wherein the fourth information comprises an indication of an aspect of the operational status of a non-fuel-related aircraft system.

7. A monitoring apparatus according to claim 6, wherein the one or more non-fuel-related systems comprises any one or more of: a flight control system; a landing gear system; a cabin environmental system; a navigational system; a powerplant system.

8. A monitoring apparatus according to claim 1, wherein the processor is configured to use a machine learning algorithm to generate the prediction.

9. A monitoring apparatus according to claim 8, wherein the machine learning algorithm is a supervised machine learning algorithm.

10. A monitoring apparatus according to claim 8, wherein the machine learning algorithm has been trained using historical first information, historical second information, historical third information, and historical fourth information relating to a historical time period; and historical fifth information indicative of a fuel quantity present in one or more fuel tanks of the aircraft over the historical time period.

11. A monitoring apparatus according to claim 10, wherein each of the historical first information, the historical third information, the historical fourth information and the historical fifth information comprises data generated by the aircraft during its operation over the historical time period or data derived from data generated by the aircraft during its operation over the historical time period.

12. A monitoring apparatus according to claim 1, wherein the aircraft comprises multiple fuel tanks and the processor is configured to generate a prediction of a quantity of fuel present in each of the multiple fuel tanks.

13. A monitoring apparatus according to claim 1, wherein the aircraft comprises multiple fuel tanks and the processor is configured to generate a prediction of a total quantity of fuel present in the aircraft.

14. A monitoring apparatus according to claim 1, wherein the processor is further configured to:
receive fifth information indicative of a fuel quantity present in one or more fuel tanks of the aircraft; and
compare the generated prediction with the received fifth information.

15. A monitoring apparatus according to claim 1, wherein the processor is further configured to detect a fault associated with a non-fuel-related system of the aircraft, based on some or all of the received first, second, third and fourth informations.

16. A method of monitoring an aircraft fuel system, the method comprising:
receiving fuel property information relating to one or more physical properties of fuel present in an aircraft;
receiving fuel system configuration information relating to the physical arrangement of a fuel system of the aircraft;
receiving orientation information relating to the physical orientation of the aircraft;
receiving aircraft systems information relating to the state of at least one non-fuel-related system of the aircraft; and
determining a fuel quantity value indicative of a quantity of fuel present in the aircraft, based on the received fuel property information, the received fuel system configuration information, and one or both of the received orientation information and the received aircraft systems information.

17. A method according to claim 16, further comprising:
receiving fuel quantity information relating to an amount of fuel present in the aircraft;
comparing the received fuel quantity information with the determined fuel quantity value; and
detecting a fuel system fault based on the results of the comparing.

18. A method according to claim 17, further comprising:
responsive to a positive detection of a fuel system fault, the fuel system using the determined fuel quantity value in place of a fuel quantity value calculated by the fuel system.

19. A method according to claim 16, further comprising:
detecting a non-fuel aircraft system fault, based on the received aircraft systems information and one or more of the received fuel property information, the received orientation information, and the received fuel quantity information.

20. An aircraft comprising a fuel system and a monitoring apparatus according to claim 1 configured to monitor the fuel system.

21. An aircraft according to claim 20, wherein the processor of the monitoring apparatus is configured to perform a method of monitoring an aircraft fuel system, the method comprising: receiving fuel property information relating to one or more physical properties of fuel present in an aircraft; receiving fuel system configuration information relating to the physical arrangement of a fuel system of the aircraft; receiving orientation information relating to the physical orientation of the aircraft; receiving aircraft systems information relating to the state of at least one non-fuel-related system of the aircraft; and determining a fuel quantity value indicative of a quantity of fuel present in the aircraft, based on the received fuel property information, the received fuel system configuration information, and one or both of the received orientation information and the received aircraft systems information.

22. A monitoring apparatus according to claim 15, wherein the processor is further configured to:
receive fifth information indicative of a fuel quantity present in one or more fuel tanks of the aircraft;
compare the generated prediction with the received fifth information; and
detect the fault associated with the non-fuel-related system based on the received fifth information.

23. An aircraft fuel system monitoring apparatus, comprising a processor configured to:
receive first information indicative of one or more parameters relating to fuel present in an aircraft;
receive second information relating to the configuration of a fuel system of the aircraft;
receive third information indicative of an orientation of the aircraft;
receive fourth information indicative of a state of one or more non-fuel-related systems of the aircraft;
generate a prediction of a quantity of fuel present in the aircraft based on the received first information, the received second information, and one or both of the received third information and the received fourth information; and,
wherein the processor is further configured to detect a fault associated with the fuel system, based on the results of a comparing generated prediction with one of the first, second, third, or fourth information.

24. A method of monitoring an aircraft fuel system, the method comprising:
receiving fuel property information relating to one or more physical properties of fuel present in an aircraft;
receiving fuel system configuration information relating to the physical arrangement of a fuel system of the aircraft;
receiving orientation information relating to the physical orientation of the aircraft;
receiving aircraft systems information relating to the state of at least one non-fuel-related system of the aircraft;
determining a fuel quantity value indicative of a quantity of fuel present in the aircraft, based on the received fuel property information, the received fuel system configuration information, and one or both of the received orientation information and the received aircraft systems information;
comparing a received fuel quantity information with a determined fuel quantity value; and
detecting a fuel system fault based on the results of the comparing.

* * * * *